United States Patent [19]  [11] 4,094,792
Bentley  [45] June 13, 1978

[54] MEMBRANE FLUID TRANSFER METHOD AND APPARATUS

[75] Inventor: Donald J. Bentley, Newport Beach, Calif.

[73] Assignee: Bentley Laboratories, Inc., Irvine, Calif.

[21] Appl. No.: 721,458

[22] Filed: Sep. 8, 1976

[51] Int. Cl.$^2$ ............................................. B01D 13/00
[52] U.S. Cl. ............................ 210/321 B; 23/258.5 M
[58] Field of Search ...................... 210/321 B, 490, 22; 23/258.5 MH, 258.5 M; 195/1.8

[56] References Cited

U.S. PATENT DOCUMENTS

| | | | |
|---|---|---|---|
| 3,332,746 | 7/1967 | Claff et al. | 23/258.5 MH |
| 3,489,647 | 1/1970 | Kolobow | 210/22 |
| 3,515,640 | 6/1970 | Rudlin | 210/321 B |
| 3,615,024 | 10/1971 | Michaels | 210/490 |
| 3,771,658 | 11/1973 | Brumfield | 23/258.5 MH |
| 3,799,873 | 3/1974 | Brown | 210/22 |
| 3,841,837 | 10/1974 | Kitrilakis et al. | 210/321 B |
| 3,998,593 | 12/1976 | Yoshida et al. | 23/258.5 MH |

OTHER PUBLICATIONS

Bramson, M. L., et al., "A New Disposal Membrane Oxygenator with Integral Heat Exchange," Journal of Thoracic & Cardiovascular Surgery, vol. 50, No. 3, Sep. 1965.

Primary Examiner—Charles N. Hart
Assistant Examiner—E. Rollins Cross
Attorney, Agent, or Firm—Lyon & Lyon

[57] ABSTRACT

A method and apparatus for fluid transfer across a membrane wherein transfer fluid is passed through the interior of a wrapped, permeable, flattened, tubular membrane and fluid to be processed is passed through passageways formed between the wrappings of the tubular membrane. The transfer fluid flow rate and pressure are maintained at a substantially constant level. In preferred embodiments the method and apparatus are utilized to oxygenate blood and/or provide for kidney dialysis.

21 Claims, 6 Drawing Figures

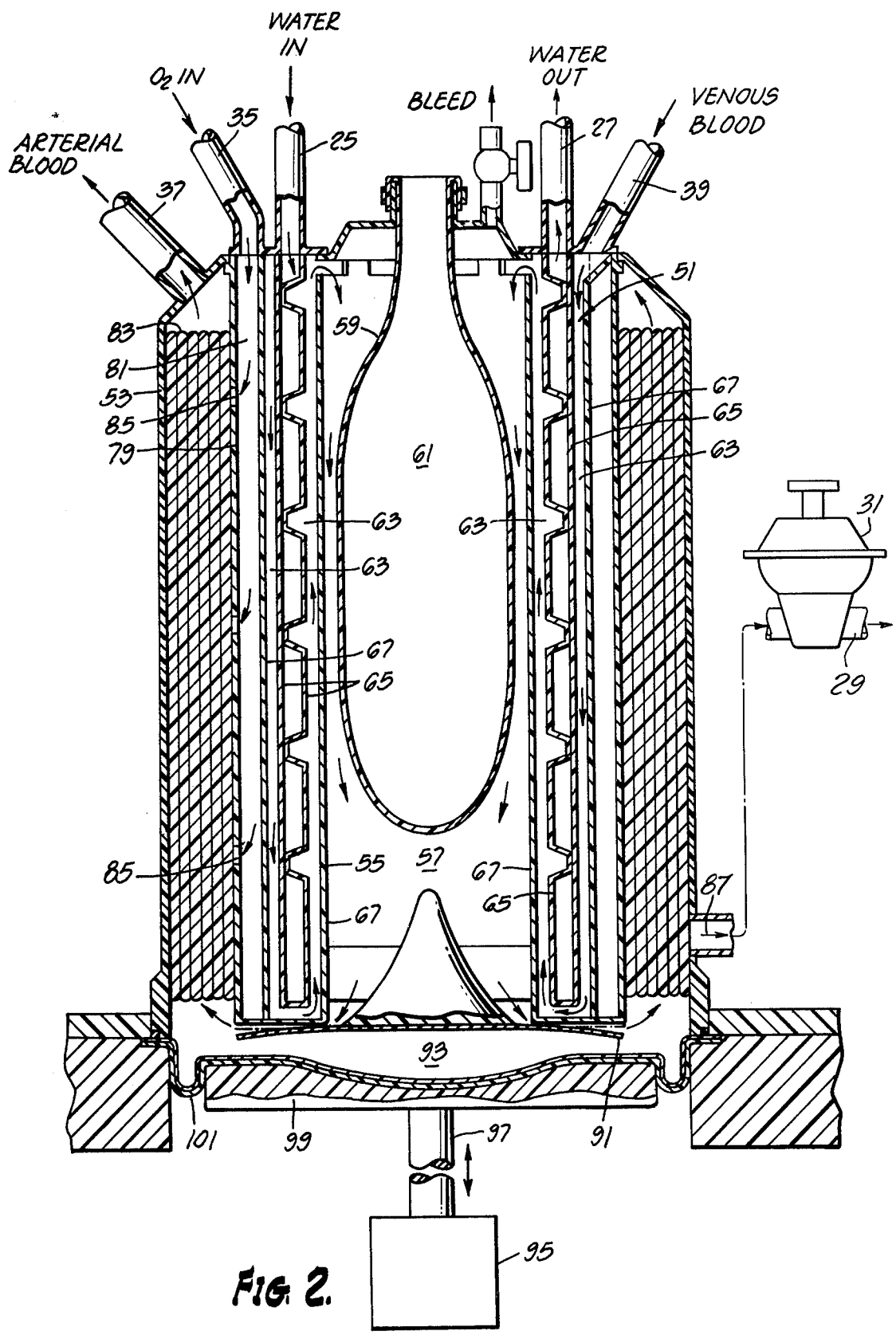

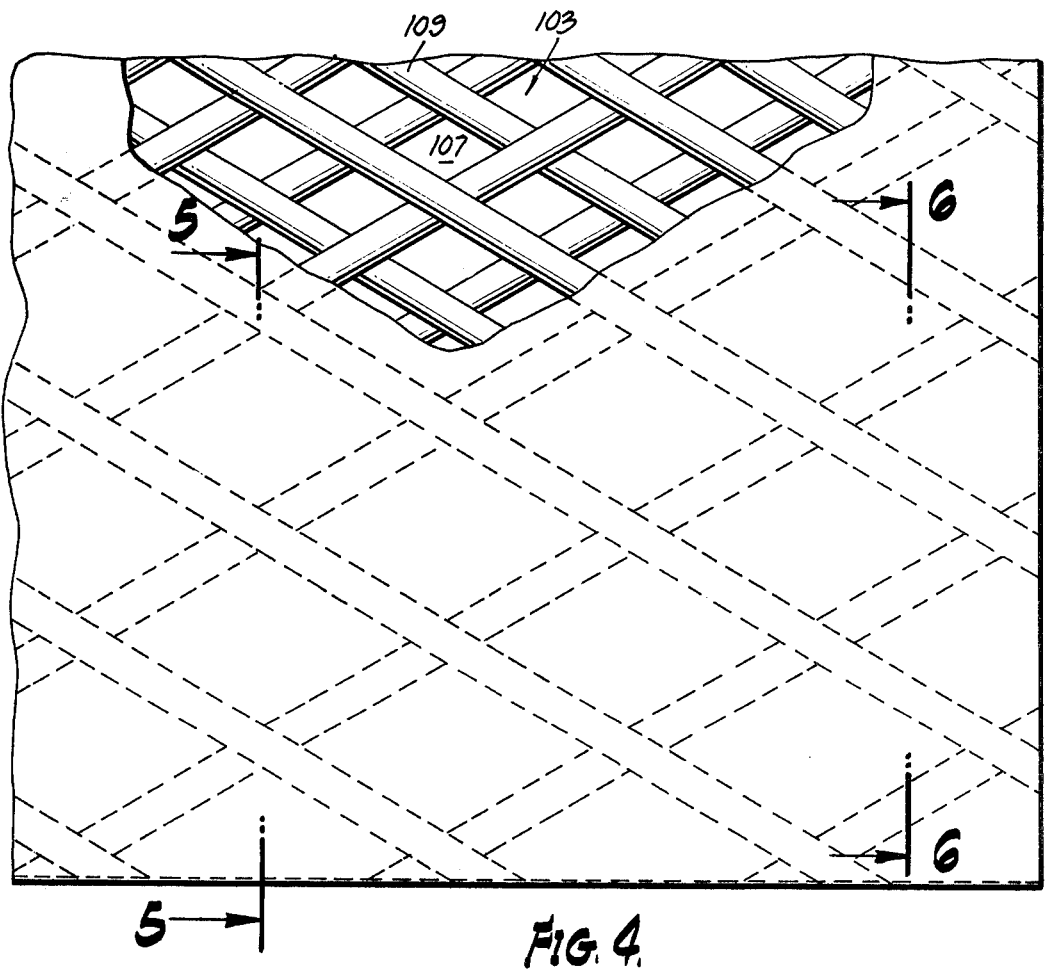
FIG. 4.
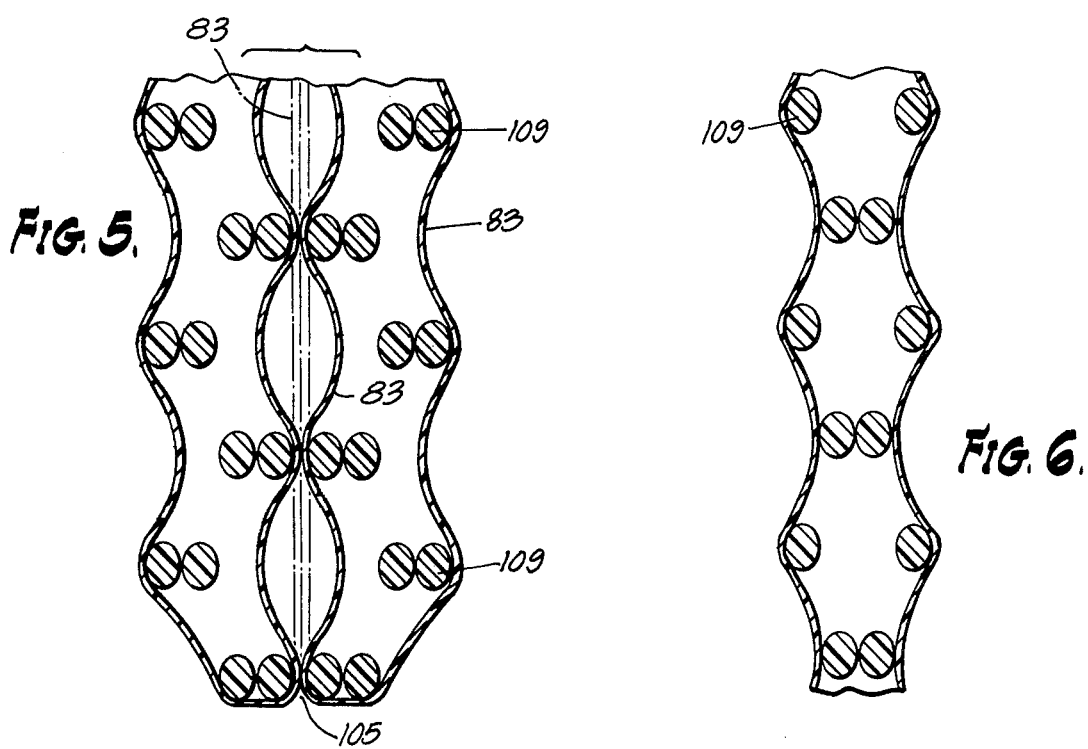
FIG. 5.
FIG. 6.

MEMBRANE FLUID TRANSFER METHOD AND APPARATUS

BACKGROUND OF THE INVENTION

1. Field of the Invention

This invention relates to a method and apparatus for fluid transfer across a membrane.

2. Description of the Prior Art

Successful extracorporeal circulation has previously been obtained by using bubble oxygenators, disc oxygenators, screen type and filming type oxygenators. All of such oxygenation devices are dependent upon a blood-gas interface in which the blood and oxygen are in intimate contact in order to achieve the necessary gas exchange whereby oxygen is transferred into the blood and carbon dioxide and other waste products are removed from the blood.

It has been hypothesized that the blood-gas interface inherent in all such designs is reponsible in part for hemolysis and protein denaturization. Such systems which are dependent upon a direct blood-gas interface are limited to a relatively short term use and are rarely used beyond an eight hour period. Thus, a need arose for the gas transfer between blood and gas without direct contact.

Indirect blood-gas transfer has been attempted across a gas permeable membrane positioned between the blood and the gas in order to reduce or minimize trauma to the blood and extend the periods of use. However, such membrane oxygenator devices have an efficiency which deteriorates with time, and are much more expensive than the earlier bubble types mentioned and are thus not used in the majority of cases except when long term support is necessary. One of the chief causes for the deterioration of the efficiency of such gas transfer membrane type oxygenators is due to the varying differential pressure across the membrane which contributes to the build-up of contaminants such as water vapor along the membrane surface on the oxygen side of the membrane and the protein, plateletts and other cells that build-up on the blood side of the membrane.

In addition, most of the prior art membrane oxygenators have been based on a silicon rubber membrane. Silicon rubber was chosen because of its permeability to oxygen and carbon dioxide in thin sections. However, silicon rubber is very difficult to deal with as it tends to stick to itself and thus requires special handling techniques which increase the cost of such devices and it is very difficult to manufacture in thin section with complete integrity. Moreover, in many of the present membrane oxygenator systems used, the blood-gas interface is not totally eliminated in that there are various reservoirs utilized in the systems which have a blood-gas interface at the surface.

SUMMARY OF THE INVENTION

In accordance with this invention a method and apparatus of modifying the properties of a fluid to be processed is provided wherein substances to be added or removed from said process fluid are transferred across a membrane. In an embodiment for the oxygenation of blood oxygen is passed through the interior of a wrapped, permeable, flattened tubular membrane and blood is passed through the passageways formed between the wrappings of the tubular membrane. The oxygen flow rate and pressure are maintained at a substantially constant level.

In a similar manner, a dialysis wash solution may be passed through the interior of a wrapped, permeable, flattened tubular membrane and blood passed through the passageways formed between the wrappings of the tubular membrane. The dialyzer wash solution flow rate and pressure are also maintained at a substantially constant level.

The blood is pumped in a pulsatile fashion through the device and to the patient's arterial system through the passageways created between adjacent membrane envelopes. The membranes are wrapped and sealed around a suitable substrate. Upon initiation of a pumping stroke the blood pressure exceeds the pressure within the membrane thus forcing the membranes apart and allowing for the passage of a thin wall of blood therebetween. As the blood pressure decreases, the maintenance of constant flow and pressure at the membrane interior forces the opposed membrane surfaces together into intimate face to face contact, thus discharging any blood contained between the membranes through an arterial outlet to the patient.

DESCRIPTION OF THE DRAWINGS

FIG. 2 is a cross-sectional view of the present invention.

FIG. 4 is a partial cross-sectional view of the present invention.

FIGS. 5 and 6 are cross-sectional views taken about 5—5 and 6—6 of FIG. 4.

DESCRIPTION OF THE PREFERRED EMBODIMENTS

Figure 1:
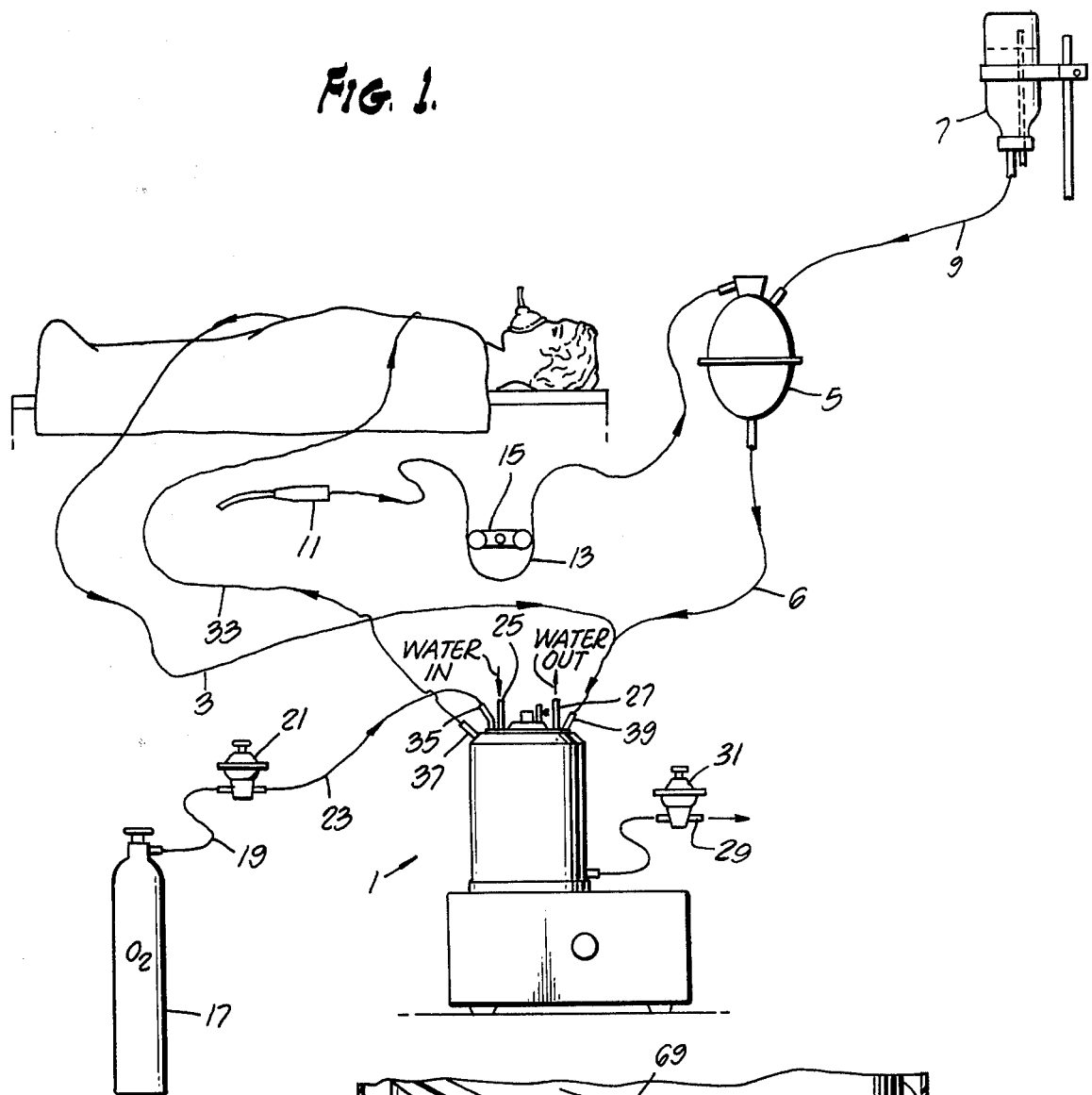
FIG. 1 is a schematic view illustrating the use of the present invention.

Referring now to FIG. 1, a device generally referred to as 1 is shown. Venous blood is shown flowing into the device 1, from the patient by means of a line 3. Additional blood flows from a cardiotomy reservoir 5 by means of line 6. For a fuller description of a cardiotomy reservoir, reference is made to my U.S. Pat. No. 3,507,395. The cardiotomy reservoir 5 may be fed from an external blood source 7 by means of a line 9 or may be extracted from a patient by means of an atraumatic fluid handling device referred to as 11 which causes blood to flow into the cardiotomy reservoir through line 13. Illustrative of a force pumping such blood through the atraumatic fluid handling device into the cardiotomy reservoir 5 is a pumping means 15.

In the embodiment wherein the device is utilized as a blood oxygenator, an oxygen source 17 passes oxygen through a line 19 into a flow control valve 21 from whence the regulated oxygen passes in to blood oxygenator 1 by means of a line 23. A heat transfer medium such as water may pass into the blood oxygenator 1 by means of an inlet 25. The heat transfer medium exits the blood oxygenator at outlet 27. The oxygen and carbon dioxide outlet is illustrated in FIG. 1 at 29, the outlet being located downstream of a pressure control means 31. The oxygenated blood is returned to a patient by means of line 33 which is connected to the oxygenator by means of a venous blood outlet 37. The oxygen inlet line at 23 is connected to the oxygenator at inlet 35 and the incoming venous blood enters the oxygenator 1 by means of a venous blood line connection 39.

Referring now to FIG. 2, a more detailed description of the blood oxygenator 1 will be given. A heat exchanger generally referred to as 51 is annularly positioned within the oxygenator housing 53 of the oxygenator 1. It is to be noted that while a heat exchanger 51 is utilized in a preferred embodiment of the method and apparatus, such a heat exchanger is not required in order to practice this invention. The inner wall 55 of the annular heat exchanger 51 forms an atrium chamber 57. In the atrium chamber 57 and occupying a portion of the chamber volume, is a flaccid, impermeable membrane enclosure 59. The interior 61 of the membrane enclosure 59 may be filled with a gaseous substance. The venous blood flows into the oxygenator 1 through venous blood inlet 39 and into a passageway to 63 formed by annular walls 65 and 67. In a preferred embodiment, the heat exchanger 51 is of a double wall construction wherein walls 67 and 65 provide for a double pass of the blood through the passage 63 in countercurrent directions. The heat transfer media, which in a preferred embodiment is water, is passed into the blood oxygenator 1 by means of inlet 25 and is removed from the oxygenator 1 by means of an outlet 37. The heat transfer media passes through the heat exchanger 51 in a double helix passage as is more clearly defined by reference to FIG. 3.

Figure 3:
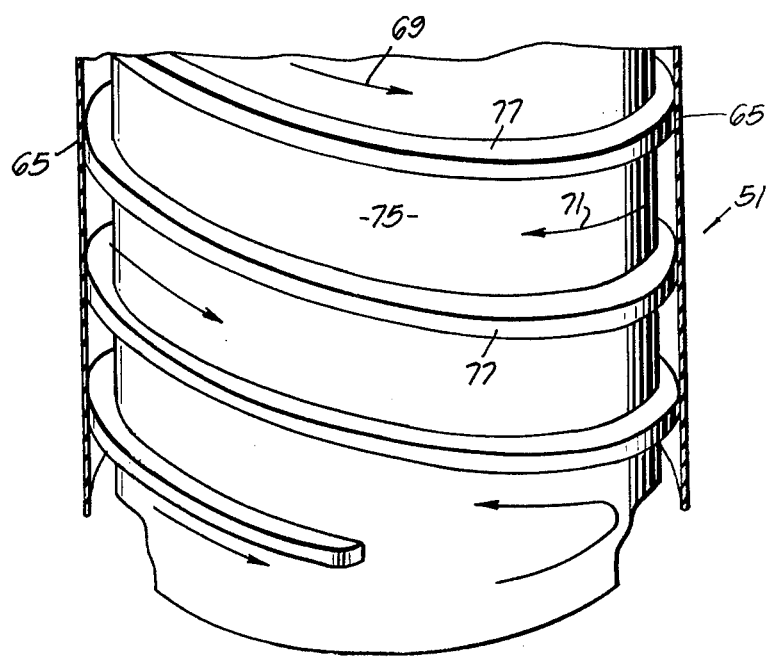
FIG. 3 is a partial cross-sectional view of the present invention.

Referring now to FIG. 3, the countercurrent heat transfer media flow produced by the double helix is illustrated by directional arrows 69 and 71 which show the heat transfer media flowing in countercurrent directions about the double helix produced by the wall member 65 and the core member 75 which has a spiral baffle 77 which separates the countercurrent heat transfer medium passages. Such a double helix design allows inlet means and outlet means at same end.

Referring again to FIG. 2, the incoming oxygen passes into the oxygenator 1 by means of oxygen inlet 35 and passes through an annular passage 81 defined by walls 79 and 67 through openings 85 into the interior of the flattened tubular membrane 83 which is spirally wrapped about wall 79 and may be enclosed at its extremity by the housing 53 of the oxygenator 1.

A leaf valve 91 may be positioned at the base of the atrium 57, the valve 91 allowing blood to flow into a ventricle 93 during the suction stroke of a reciprocating piston 97 driven by a driving means 95. The ventricle 93 is partially formed by a flaccid, impermeable membrane 101 adapted about a diaphragm 99 which may be mounted on shaft 97.

The tubular membrane 83 is preferably formed from an asymetric, thermoplastic material having permeability to oxygen and carbon dioxide. Other membranes with appropriate permeability may also be used. The wrapper tubular membrane 83 is preferably potted or otherwise adhered to the walls 53 and 79 and a plurality of holes are provided such as at 85 and 87 to allow for the entrance and exit of the gas respectively. A back pressure regulator 31 regulates the exit of excess oxygen and the carbon dioxide removed from the blood.

Referring now to FIGS. 4–6, a membrane support structure generally referred to as 103 is shown. The membrane is permanently deformed into the interstices 107 of the fibers 109 of the support structure 103 whereby forming a plurality sinuous passageway 105 between the alternate wrappings of the tubular membrane 83. Such a configuration increases the membrane transfer area and creates turbulence in the fluids on either side of the membrane 83 which aids in the transfer. Referring again to FIG. 2, it is understood that any suitable membrane support structure 103, such as an embossed sheet, having a plurality of interstices 107 may be utilized in accordance with this invention.

The system functions as follows:

The oxygen flow control valve 21 is adjusted to maintain an appropriate, constant flow of oxygen into the oxygenator through inlet 35. The pressure means, or back pressure regulator 31, is adjusted to maintain a pressure on the oxygen side of the membrane. This constant oxygen pressure is sufficient to force the membranes 83 which comprise the blood passage together into intimate face to face contact as shown by the dashed lines of FIG. 5.

When the upward stroke of the reciprocating piston 97 is initiated, valve 91 is closed and the pressure within the ventricle 93 forces the membranes 83 apart progressively as shown by the solid lines of FIG. 5. The blood transverses the membrane passage 105 in a gentle, turbulent fashion, due to the variable pressure and velocity profile of the blood pulse, toward the arterial discharge port 37 of the device 1. As the ventricle actuating means 97 reaches the top of its stroke, the blood continues to travel through the blood passages 105 between the membranes toward the arterial outlet 97 due to kinetic energy causing the pressure at the inlet to the blood passages 105, between the membranes 83, from the ventricle 93, to be reduced allowing the gas pressure on the inside of the membrane 83 created by the back pressure on the inside of the membrane 83 created by the back pressure of regulator 31 to force the membrane 83 comprising the blood passage 105 tightly together in face to face contact creating a seal in the blood passage between the membranes 83 at the inlet. The gas pressure continues to force the membranes 83 progressively together from bottom to top discharging the blood between the membranes 83 through the arterial outlet fitting 37 and thence to the patient by means of line 33. On the next suction stroke of the actuator 97 the ventricle 93 fills in the previously described manner and the process is repeated. There is no venous back flow pulse in the device 1.

The advantages to the above described arrangement are that it is simple to adjust and operate and the maximum net through put of blood for the device will be increased. The blood thickness in the blood passages between the membranes is minimized, therefore, the efficiency of transfer through the membranes to the blood is increased. The apparatus and method when utilizing the device 1 as a kidney dialyzer is substantially similar to its operation as an oxygenator, however, an atrium and ventricle are not required; a dialyzer wash solution follows the oxygen flow path and excess dialyzer wash solution and impurities removed from the blood follow the excess oxygen and carbon dioxide flow path.

As the blood pressure is greater than the pressure of the fluid within the membrane as blood is passing between the membranes, there is no possibility of leakage of the fluid contained within the membrane into the blood stream. When the gas or dialysate medium pressure exceeds the blood pressure, the blood passage is closed and the pressure on the opposed membranes counteract each other.

It is understood that other variations of the specific construction and arrangement of the system disclosed above may be made by those skilled in the art without departing from the invention as defined in the appended claims.

What is claimed is:

1. A membrane fluid transfer device comprising:
   a housing having a process fluid inlet and outlet;
   an atrium chamber means for providing a reservoir for incoming fluid formed within said housing and in communication with said housing process fluid inlet;
   a spirally wound, flattened, tubular permeable membrane having a transfer fluid inlet at one end of said tubular membrane and a transfer fluid outlet at the opposite end of said membrane, said membrane forming passageways between adjacent windings of said membrane, one end of said passageways being in communication with said ventricle and the opposite end of said passageways being in communication with said housing process fluid outlet;
   control means for maintaining a substantially constant transfer fluid flow in communication with said transfer fluid inlet;
   control means for maintaining a substantially constant transfer fluid pressure in communication with said transfer fluid outlet; and a ventricle means for pumping fluid to be treated through said passageways between said adjacent windings of said membrane, said ventricle means being connected to said atrium by a fluid passageway having a valving means positioned within said fluid passageway, said membrane windings and a portion of said ventricle being formed by a member adapted to be actuated by a driving means, whereby the pressure of the fluid to be treated is pumped alternately from a pressure lower than the controlled and constant transfer fluid pressure to a pressure higher than the controlled transfer fluid pressure and thus allowing for alternately opening and closing of said passageways between said adjacent windings of said membrane.

2. A membrane oxygenator comprising:
   a housing having a blood inlet and outlet;
   an atrium chamber means for providing a reservoir for incoming fluid formed within said housing and in communication with said housing blood inlet;
   a flaccid, impermeable membrane enclosure occupying a portion of said atrium;
   a spirally wound, flattened, tubular permeable membrane having an oxygen inlet at one end of said tubular membrane and an oxygen and carbon dioxide outlet at the opposite end of said membrane, said membrane forming passageways between adjacent windings of said membrane, one end of said passageways being in communication with said ventricle and the opposite end of said passageways being in communication with said housing blood outlet;
   control means for maintaining a substantially constant oxygen and carbon dioxide transfer oxygen flow in communication with said inlet;
   control means for maintaining a substantially constant oxygen and carbon dioxide pressure in communication with said outlet; and
   a ventricle means for pumping said blood through said passageways between said adjacent windings of said membrane, said ventricle means being connected to said atrium by a fluid passageway having a valving means positioned within said fluid passageway, said membrane windings and a portion of said ventricle being formed by a member adopted to be actuated by a driving means, whereby the pressure of said blood is pumped alternately from a pressure lower than the controlled and constant oxygen and carbon dioxide pressure to a pressure higher than the controlled oxygen and carbon dioxide pressure and thus allowing for alternately opening and of closing said passageways between said adjacent windings of said membrane.

3. The membrane oxygenator claimed in claim 2 wherein said atrium membrane enclosure is filled with a gas at atmospheric pressure.

4. The membrane oxygenator claimed in claim 3 wherein said gas is substantially carbon dioxide, and said carbon dioxide is maintained at a pressure above atmospheric pressure.

5. The membrane oxygenator claimed in claim 2 wherein said ventricle valving means is defined as comprising an annular leaf valve.

6. The membrane oxygenator claimed in claim 2 wherein the area between said ventricle and said driving means is vented.

7. The membrane oxygenator claimed in claim 6 wherein said driving means is furhter defined as reciprocating between said pressure stroke and a suction stroke.

8. The membrane oxygenator claimed in claim 2 wherein said tubular membrane is formed from an asymetric, thermoplastic material.

9. The membrane oxygenator claimed in claim 8 wherein said tubular membrane material is selected from the group consisting of polysulphane, polycarbonate and copolymers thereof.

10. The fluid transfer device claimed in claim 1 wherein said tubular membrane is further defined as having a multi-interstice support structure positioned within said tubular membrane.

11. The membrane oxygenator claimed in claim 10 wherein said tubular membrane is permanently deformed into said support structure interstices.

12. A membrane oxygenator comprising:
    a housing having an annular heat exchanger positioned therein, said heat exchanger having a heat transfer medium inlet and outlet and a blood inlet and outlet;
    an atrium chamber means for providing a reservoir for incoming fluid formed by the inner surface of said heat exchanger, a flaccid, impermeable membrane enclosure occupying a portion of said atrium, and said atrium being in communication with said heat exchanger blood outlet;
    an arterial blood outlet;
    a spirally wound, flattened tubular permeable membrane having an oxygen inlet at one end of said tubular membrane and an oxygen and carbon dioxide outlet at the opposite end of said membrane, said membrane being positioned between the inner surface of said housing and the outer surface of said heat exchanger and forming passageways between adjacent windings of said membrane, one end of said passageways being in communication with said ventricle and the opposite end of said passageways being in communication with said arterial blood outlet;
    control means for maintaining a substantially constant oxygen and carbon dioxide transfer oxygen flow in communication with said inlet;
    control means for maintaining a substantially constant oxygen and carbon dioxide pressure in communication with said outlet; and a ventricle means for pumping said blood through said passageways between said adjacent windings of said membrane, said ventricle means being connected to said atrium by a fluid passageway having a valving means positioned within said fluid passageway, said membrane windings and a portion of said ventricle being formed by a member adopted to be actuated by a driving means, whereby the pressure of said blood is pumped alternately from a pressure lower than the controlled and constant oxygen and carbon dioxide pressure to a pressure higher than the controlled oxygen and carbon dioxide pressure and thus allowing for alternating opening and of closing said passageways between said adjacent windings of said membrane.

13. The membrane oxygenator claimed in claim 12 wherein said heat exchanger is further defined as being a double walled, double helix heat exchanger.

14. A membrane oxygenator comprising:
a housing having an annular double walled helix heat exchanger positioned therein, said heat exchanger having a heat transfer medium inlet and outlet and a blood inlet and outlet;
an atrium chamber means for providing a reservoir for incoming fluid formed by the inner surfaces of said heat exchanger and a flaccid, impermeable membrane enclosure occupying a portion of the atrium volume, said atrium being further defined as being in communication with said heat exchanger blood outlet;
an arterial blood outlet;
a spirally wound, flattened tubular permeable membrane positioned within the inner surface of said housing and the outer surface of said heat exchanger, said tubular membrane having a multi-interstice support structure positioned within said tubular membrane and said membrane being deformed into said support structure interstice, said wound tubular membrane forming passages between adjacent windings of said membrane, one end of said passageways being in communication with said ventricle and the opposite end of said passageways being in communication with said arterial blood outlet, said tubular membrane being further defined as having an oxygen inlet at one end of said tubular membrane and a valve oxygen and carbon dioxide outlet at the opposite end of said membrane;
control means for maintaining a substantially constant oxygen and carbon dioxide transfer oxygen flow in communication with said inlet;
control means for maintaining a substantially constant oxygen and carbon dioxide pressure in communication with said outlet; and a ventricle means for pumping said blood through said passageways between said adjacent windings of said membrane, said ventricle means being connected to said atrium by a fluid passageway having a valving means positioned within said fluid passageway, said membrane windings and a portion of said ventricle being formed by a member adapted to be actuated by a driving means, whereby the pressure of said blood is pumped alternately from a pressure lower than the controlled and constant oxygen and carbon dioxide pressure to a pressure higher than the controlled oxygen and carbon dioxide pressure and thus allowing for alternately opening and of closing said passageways between said adjacent windings of said membrane.

15. The membrane oxygenator claimed in claim 13 wherein said atrium membrane enclosure is charged with carbon dioxide to a pressure above atmospheric pressure.

16. The membrane oxygenator claimed in claim 14 wherein the area between said ventricle and said driving means is vented to the atmosphere.

17. A membrane oxygenator comprising:
a housing having an annular double wall heat exchanger positioned therein, said heat exchanger having a heat transfer medium inlet and outlet and a blood inlet and outlet;
an atrium chamber means for providing a reservoir for incoming fluid formed by the inner wall of said heat exchanger, a flaccid, impermeable membrane enclosure occupying a portion of said atrium, and said atrium being in communication with said heat exchanger blood outlet;
a spirally wound, flattened, tubular, permeable membrane having an oxygen inlet at one end of said tubular membrane and a valved oxygen and carbon dioxide outlet at the opposite end of said membrane, said membrane being formed from a thermoplastic material selected from the group consisting of polysulfone, polycarbonate and copolymers thereof, said tubular membrane being further defined as having a multi-interstice support structure positioned within said tubular membrane and said tubular membrane being permanently deformed into said support structure interstices, said supported tubular membrane being positioned between the inner surface of said housing and the outer surface of said heat exchanger and forming passageways between adjacent windings of said membrane, one end of said passageways being in communication with said ventricle and the opposite end of said passageways being in communication with said arterial blood outlet;
control means for maintaining a substantially constant oxygen and carbon dioxide transfer oxygen flow in communication with said inlet;
control means for maintaining a substantially constant oxygen and carbon dioxide pressure in communication with said outlet; and
a ventricle means for pumping said blood through said passageways between said adjacent windings of said membrane, said ventricle means being connected to said atrium by a fluid passageway having a valving means positioned within said fluid passageway, said membrane windings and a portion of said ventricle being formed by a member adopted to be actuated by a driving means, whereby the pressure of said blood is pumped alternately from a pressure lower than the controlled and constant oxygen and carbon dioxide pressure to a pressure higher than the controlled oxygen and carbon dioxide pressure and thus allowing for alternately opening and of closing said passageways between said adjacent windings of said membrane.

18. A membrane oxygenator comprising:
a housing having a blood inlet and outlet;
an atrium chamber means for providing a reservoir for incoming fluid formed within said housing and in communication with said housing blood inlet;
a spirally wound, flattened, tubular permeable membrane having an oxygen inlet at one end of said tubular membrane and a valved oxygen and carbon dioxide outlet at the opposite end of said membrane, said membrane forming passageways between adjacent windings of said membrane, one end of said passageways being in communication with said ventricle and the opposite end of said passageways being in communication with said housing blood outlet;

control means for maintaining a substantially constant oxygen and carbon dioxide transfer oxygen flow in communication with said inlet;

control means for maintaining a substantially constant oxygen and carbon dioxide pressure in communication with said outlet; and a ventricle means for pumping said blood through said passageways between said adjacent windings of said membrane, said ventricle means being connected to said atrium by a fluid passageway having a valving means positioned within said fluid passageway, said membrane windings and a portion of said ventricle being formed by a member adopted to be actuated by a driving means, whereby the pressure of said blood is pumped alternately from a pressure lower than the controlled and constant oxygen and carbon dioxide pressure to a pressure higher than the controlled oxygen and carbon dioxide pressure and thus allowing for alternately opening and of closing said passageways between said adjacent windings of said membrane.

19. A membrane dialyzer comprising:

a housing having a blood inlet and outlet and a dialyzer wash solution inlet and outlet;

a spirally wound, flattened, tubular permeable membrane having a dialyzer wash solution inlet at one end of said tubular membrane and a valve excess dialyzer wash solution and blood impurities outlet at the opposite end of said membrane, said membrane forming passageways between adjacent windings of said membrane, one end of said passageways being in communication with said housing blood inlet and the opposite end of said passageways being in communication with said housing blood outlet;

control means for maintaining a constant dialyzer wash solution flow in communication with said dialyzer wash solution inlet;

control means for maintaining a constant dialyzer wash solution pressure in communication with said dialyzer wash solution and blood impurities outlet; and a ventricle means for pumping said blood through said passageways between said adjacent windings of said membrane, said ventricle means being connected to said blood inlet by a fluid passageway, said membrane windings and a portion of said ventricle being formed by a member adopted to be actuated by a driving means, whereby the pressure of said blood is pumped alternately from a pressure lower than the controlled and constant dialyzer wash solution pressure to a pressure higher than the controlled dialyzer wash solution pressure and thus allowing for alternately opening and of closing said passageways between said adjacent windings of said membrane.

20. A method for dialyzing blood across a membrane comprising:

forcing a dialyzer wash solution into the interior of said wrapped oxygenating membrane;

removing blood impurities from said blood across said membrane;

maintaining a substantially constant dialyzer wash solution flow;

maintaining a substantially constant dialyzer wash solution pressure; and pumping said blood to be processed alternating from a pressure lower than the controlled and constant dialyzer wash solution pressure to a pressure higher than the controlled dialyzer wash solution pressure and thus allowing for alternating opening and closing of said passageways between said adjacent windings of said membrane.

21. The method of dialyzing blood across a membrane claimed in claim 20 wherein said method is further defined as producing turbulence of said pumping of said blood to be dialyzed by passing said blood over and through membrane covered multi-interstice passageways with a continuously varying velocity and pressure pulse profile.

* * * * *